United States Patent [19]

Sugier et al.

[11] 4,346,179

[45] Aug. 24, 1982

[54] PRODUCTION OF ALCOHOLS FROM SYNTHESIS GASES

[75] Inventors: Andre Sugier; Edouard Freund; Jean-François Le Page, all of Rueil Malmaison, France

[73] Assignee: Institut Francais du Petrole, Rueil-Malmaison, France

[21] Appl. No.: 137,098

[22] Filed: Apr. 4, 1980

[30] Foreign Application Priority Data

Apr. 5, 1979 [FR] France ............................... 79 08881

[51] Int. Cl.³ ..................... C07C 27/06; C07C 31/02; C07C 31/04
[52] U.S. Cl. .................................. 518/707; 518/706; 518/713; 518/705; 518/712; 568/902
[58] Field of Search ............ 260/449.5, 449 R, 449 S; 568/902; 518/707, 706, 705

[56] References Cited

U.S. PATENT DOCUMENTS

| | | | |
|---|---|---|---|
| 1,859,244 | 5/1932 | Patart | 260/449 |
| 1,959,219 | 5/1934 | Reed | 260/499 R |
| 2,623,906 | 12/1952 | Gresham | 568/902 |
| 2,787,628 | 4/1957 | Himmler et al. | 260/449.5 X |
| 4,122,110 | 10/1978 | Sugier et al. | 260/449.5 |
| 4,226,795 | 10/1980 | Bowman | 260/449.5 |

FOREIGN PATENT DOCUMENTS 1046822  12/1953  France ............................ 260/449 R

*Primary Examiner*—Howard T. Mars
*Attorney, Agent, or Firm*—Millen & White

[57] ABSTRACT

Process for manufacturing a constituent for motor car gasoline from a synthesis gas containing essentially carbon dioxide, carbon monoxide and hydrogen, comprising producing methanol and its higher homologs by treatment of said synthesis gas in a first catalytic reaction zone at 230°–350° C., cooling and condensing the effluent therefrom, separating from the liquid condensate a gas fraction, treating the latter at 240°–300° C. in a second catalytic reaction zone to produce a liquid methanol fraction and admixing said methanol fraction with said liquid condensate to form said gasoline constituent.

20 Claims, 1 Drawing Figure

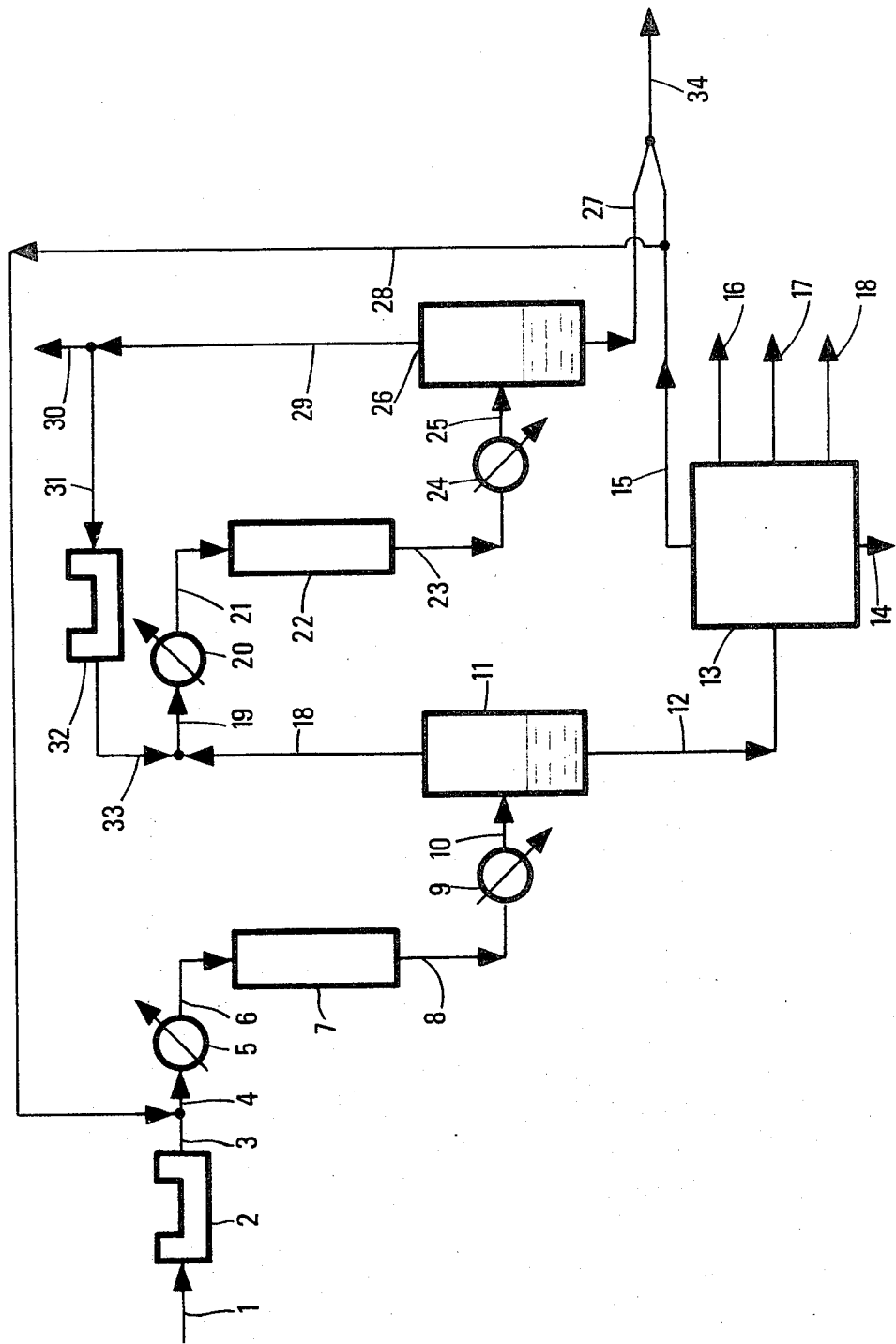

PRODUCTION OF ALCOHOLS FROM SYNTHESIS GASES

SUMMARY OF THE INVENTION

This invention concerns a process for producing a mixture of methanol and higher homolog alcohols, particularly ethanol and propanol, said mixture having the property, in view of its composition, of being directly usable, in addition to gasoline, so as to obtain a motor gasoline of moderate price. The invention is characterized by the coupling of two catalytic reaction zones destined to the treatment of a synthesis gas ($CO + CO_2 + H_2$). The first catalytic reaction zone produces mainly ethanol, propanol, methanol and, to a lesser extent, butanol, pentanol and a few other alcohols; the residual gases from the first reaction zone, whose composition is substantially similar to that of the synthesis gas used as charge in the first reaction zone, (as a result of the particular operating conditions used in the first reaction zone) are fed to a second catalytic reaction zone, to produce methanol. The effluents from the two reaction zones may be separately collected, but are preferably recovered together since the resulting mixture contains an ideal proportion of methanol and higher homolog alcohols and consequently can be added as such to a gasoline fraction so as to form a convenient gasoline, for example for motor cars, at a moderate price, this ideal mixture containing, by weight, about from 74 to 90% of methanol and from 10 to 26% of a mixture of higher homolog alcohols consisting in major part of ethanol and propanol.

Thus, the present invention concerns a chain of processes for producing methanol and its saturated and linear primary higher homologs from synthesis gas containing essentially CO, $CO_2$ and $H_2$.

BACKGROUND OF THE INVENTION

It must be recalled that in addition to the methanol synthesis, which produces selectively this alcohol, two types of procesess have been mainly proposed for the preparation of alcohols from a synthesis gas of $CO + H_2$: the Fischer and Tropsch synthesis and the isobutylic synthesis.

As a general rule, the processes of the Fischer and Tropsch type are not very selective; there is obtained a mixture of olefinic, paraffinic and oxygenated products over a very wide range of molecular weights. Moreover, the productivity of the catalyst is very low, generally lower than 5 kg of products per ton of catalyst and per hour.

As concerns the isobutylic synthesis, performed in Europe from 1935 to 1945, it derives from the methanol synthesis by the use of the same catalyst (zinc chromite) modified by the addition of an alkaline salt, but it is operated under higher pressures and temperatures (respectively 300 to 400 bars, 380° to 450° C.); a representative composition by weight of the products obtained is as follows: methanol (50%), isobutanol (20-40%), n-propanol and higher alcohols (complement to 100%); the higher alcohols consist of primary and secondary (50-50%) non linear alcohols.

Processes of the prior art are used to produce, in at least two reactors in series, an alcohol (usually methanol) or a mixture of alcohols, from a synthesis gas (French Pat. No. 1,046,822, Patent of the Federal Republic of Germany Pat. No. 1,257,762 and U.S. Pat. No. 1,959,219); but these processes always comprise a recycling to the first reactor of at least one portion of the residual gases from one or more reactors, this recycling being performed in order to increase the yield of alcohol(s) in the first reactor but having the disadvantage of resulting in further investment expenses. The process of the invention, on the contrary, does not require this costly recycling since it has precisely for objet to avoid the production of a too large amount of linear and saturated higher homologs of methanol in the first reaction zone in view of the fact that the desired final mixture of methanol with homolog alcohols should have a content of homolog alcohols not exceeding 26% by weight. Briefly stated, this invention proposes a combination of processes where, to a synthesis of methanol is coupled a synthesis of homolog alcohols.

BRIEF DESCRIPTION OF THE DRAWING

The FIGURE is a schematic diagram of an embodiment of the invention.

DETAILED DISCUSSION

In conformity, for example, with the simplified diagram of the accompanying drawing, such a device, which does not comprise a recycling of the gas to the synthesis reactor of the homolog alcohols, provides for the production at low price of variable proportions of ethanol, propanol and butanol, adaptable to the market requirements. The conversion of CO in the first catalytic reaction zone (where are manufactured the homolog alcohols) is from 7 to 40% or may be from 10 to 25% with respect to the gas feed at the inlet of said first reaction zone.

The synthesis gas is introduced through line 1 into compressor 2 and then, through lines 3 and 4, it is heated in a heat exchange system 5 up to the inlet temperature in reactor 7 where the synthesis gas is introduced through line 6. The synthesis of methanol and its higher homologs is performed in the first catalytic reaction zone represented by reactor 7. The effluent from reactor 7 is withdrawn therefrom through line 8 and cooled in zone 9 where are condensed the liquid products. The effluent from zone 9 is then fed, through line 10, to a condensation zone (liquid-gas separation zone) 11. The liquid fraction is conveyed, through line 12, to the separation section 13, wherefrom are separately recovered water (from line 14 at the bottom of the column) and alcohols. On the FIGURE, separate lines are shown for withdrawing the different main alcohols formed. Thus there is withdrawn methanol (through line 15 at the top of the column), ethanol (through line 16) propanol (through line 17) and butanol (through line 18). At least a portion of the methanol from line 15 is optionally admixed, in line 34, with the methanol issued, through lines 27, 25 and 23, from the second catalytic zone 22 of methanol synthesis. But, in a generally preferred manner, there is recovered simultaneously in the same line, methanol, ethanol, propanol and optionally butanol and the other formed alcohols such as isopropanol, pentanol and isobutanol (generally the isobutanol amount in the final mixture is not higher than 2 to 3% by weight) to admix these alcohols directly with methanol from line 27, in order to obtain a mixture which can be added as such to gasoline.

The gas fraction, withdrawn from separator 11, is fed, through lines 18 and 19 to the heating zone 20, without intermediary recompression; compressor 2 is thus the only common compressor for the two reactors 7 and 22 of the process of the invention; accordingly, the pressure in reactor 22 is substantially close to that prevailing in reactor 7, to the extent that the pressure drops are not considered. The gas fraction is then fed, at least partly, through line 21 to the second catalytic reaction zone corresponding to reactor 22 where methanol synthesis is effected; the products issued from this reactor, through line 23, are cooled in zone 24 to condense methanol, these products being then introduced, through line 25, into the gas liquid separator 26, wherefrom methanol is withdrawn through line 27.

In reactor 22, the liquid effluent of the produced alcohols contains generally, by weight, at least 97% and preferably at least 98.5% of methanol.

Unconverted gas is withdrawn from the separator 26 through line 29. Optionally, and preferably, a portion at least of this gas is fed, through line 31, to the recycling compressor 32 and then is recycled, as shown on the FIGURE, through lines 33, 19 and 21 to the reactor 22. At least another portion of the gas from line 29 is optionally purged, by means of line 30, the purge gas containing mainly CO, $CO_2$, hydrogen and nitrogen. This recycling of a portion of the unconverted gas from line 29 to the second reactor 22 may be performed, at the outlet of compressor 32, not through line 32, as shown on the FIGURE, but directly from the output of compressor 32, to reactor 22 through one or more lines (not shown on the drawing) which open at different levels of the reactor and thus are used to produce a quench.

Optionally, and preferably, when it is desired to increase the production of homolog alcohols in order to obtain an ideal mixture, containing for example, by weight, from 13 to 21% of homolog alcohols, (proportion varying according to the specific desired applications), there is recycled, at the end of the process according to the invention, at least one of the alcohols produced in the process and, for example, either at least one portion of the methanol produced in the first or the second reactor (in the FIGURE, this is shown as a portion of the methanol from line 15 withdrawn through line 28), or a portion of the methanol withdrawn from the total mixture of the alcohols produced in both reactors 7 and 22 (recycling not shown on the FIGURE), or a mixture of methanol and ethanol or of methanol, ethanol and/or other homolog alcohols, withdrawn from the mixture of the alcohols produced in the catalytic synthesis zone of homolog alcohols or withdrawn from the total mixture of the alcohols produced in both reactors 7 and 22 (recycling not shown on the FIGURE) or a portion of the total mixture of the alcohols produced in both reactors 7 and 22 (recycling not shown on the FIGURE) or a portion of at least one homolog alcohol withdrawn before or after making the mixture of all the alcohols produced by the process of the invention. Generally, there is recycled, by weight, from 1 to 20% of methanol and/or 0.1 to 8% of at least one homolog alcohol, with respect to the total amount of alcohols produced in the process.

In an alternative embodiment, not illustrated, of the above-described flow-sheet, the synthesis of methanol homologs is no longer performed in a single reactor 7, but in at least two reactors and preferably in two reactors arranged in series, with an intermediary separation of the homolog alcohols which inhibit their own synthesis. The conversion rate of CO in each of the reactors in series remains in the range from 7 to 40% or from 10 to 25% with respect to the gas feed at the inlet of each reactor. This arrangement makes it possible to multiply the production of homolog alcohols by a factor of from 1.8 to 2.

In general, in the process of the invention, the composition of the residual gas withdrawn from the one or more reactors for the synthesis of methanol higher homolog alcohols, is very substantially similar to that of the initial synthesis gas. Preferably, this residual gas is fed to the methanol reactor in admixture with at least one portion of the gases withdrawn from the methanol synthesis reactor. The gases are mixed either before their admission into the reactor, or in the reactor itself, where the recycled gases withdrawn from the methanol synthesis reactor is introduced as quench. However, this admixing operation is not equivalent to a dilution of the residual gas issued from the one or more synthesis reactors of homolog alcohols since the recycling gas of the methanol reactor does not amount, by volume, to more than 10% of the volume of the residual gas from the one or more reactors for the synthesis of methanol homolog alcohols.

According to the invention, the molar ratio $H_2/(CO+CO_2)$ in the initial synthesis gas, is from 0.5 to 4, preferably from 0.7 to 3.5, the molar ratio $H_2/CO$ being itself preferably from 1.0 to 4.0. The synthesis reaction of methanol higher homolog alcohols is performed under pressures varying from 30 to 150 bars and preferably from 50 to 120 bars, at temperatures from 230° to 350° C. and preferably from 250° to 320° C., at space velocities from 1 000 to 10 000, preferably, from 2 000 to 6 000, expressed in m³ (N.T.P.) of synthesis gas per m³ of catalyst and per hour.

The operation is conducted with the catalysts already described for this type of reaction but, preferably, with the catalysts disclosed in the French Pat. No. 2,369,234 which contain at least 4 essential elements consisting of copper, cobalt, at least one metal M selected from the group consisting of chromium, iron, vanadium, manganese and a rare earth, and at least one metal A which is an alkali metal, preferably lithium, sodium or potassium. Optionally zinc may also be present in the catalyst. These elements are used in the following atomic proportions:

$Cu_xCo_yM_zA_v$

When zinc is present, its atomic proportion is $Zn_u$.

The metals of these catalysts may be deposited on a carrier, for example alumina or calcium aluminate. This carrier may be admixed to the metal salts solution before the precipitation.

In this general formula, x has a value from 0.1 to 1, y a value from 0.1 to 1 and preferably from 0.1 to 0.6, z a value from 0.2 to 1, u a value from 0 to 0.5 but not exceeding 0.5 y, and v a value from 0.001 to 0.25 times the sum (x+y+z). In the preferred catalyst formula, the proportions are x=1, y=0.2 to 1.2, z=0.1 to 1 and v=0.02 to 0.2. In these formulas, z and v correspond to the total value of the concentrations of metals M and A when several metals M and/or A are present. The above formulas do not indicate the form in which the metals are present. As a general rule, at the end of the manufacture of the catalyst, these metals are present for example, as oxides but, during the operation, certain oxides may be reduced to a certain extent. The catalysts are in the form of pellets, pills, extrudates or crushed materials having an average equivalent diameter from 2 to 6 mm.

With the catalysts recommended in the French Pat. No. 2,369,234 and in the above-mentioned operating conditions, the conversion rate of the CO contained in the synthesis gas remains at a low level (10 to 20%) as a result of the strong inhibition by the reaction products.

The methanol synthesis reaction is conducted at a temperature preferably from 240° to 300° C. under an operating pressure from 50 to 120 bars, at space velocity from 5 000 to 20 000 m³ of synthesis gas at normal temperature and pressure (N.T.P.) per m³ of catalyst and per hour and with a molar ratio $H_2/(CO+CO_2)$ from 1.5 to 10. The catalyst is a conventional one but the synthesis of methanol is preferably conducted with a catalyst containing copper, cobalt, zinc and at least one metal M present in the following atomic proportions: $Cu_{x'}Co_{y'}Zn_{u'}M_{z'}$ wherein M designates one or more elements selected from chromium, iron, vanadium, manganese and a rare earth, and where, generally, $x'$ varies from 0.1 to 1, $y'$ from 0.01 to 0.2, $u'$ from 0.1 to 1 and $z'$ from 0.2 to 2; the metals may be present, for example, as oxides. These metals may be deposited on a carrier, for example a carrier containing alumina.

Preferably, the operation in the synthesis reactor(s) of methanol higher homolog alcohols, is conducted at a temperature $T_1$ from 265° to 300° C. and, in the methanol synthesis reactor, at a temperature $T_2$ from 260° to 270° C., the temperature $T_2$ being lower by about 5° to 30° C. than temperature $T_1$.

EXAMPLE 1

There is used, for the synthesis of homolog alcohols, a catalyst where the metals are present in the following molar proportions:

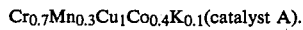

$Cr_{0.7}Mn_{0.3}Cu_1Co_{0.4}K_{0.1}$(catalyst A).

The catalyst is prepared from a citric acid solution containing the suitable proportions of chromic anhydride, copper nitrate, manganese nitrate, cobalt carbonate; the solution is dried at 200° C. and then roasted in air at 450° C.; the resulting powder is pelletized to pellets of a 5 mm diameter and a 5 mm height and the pellets are impregnated with a potassium hydroxide solution.

For the synthesis of methanol, there is used a catalyst where the metals are present in the following molar proportions:

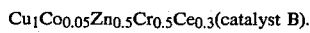

$Cu_1Co_{0.05}Zn_{0.5}Cr_{0.5}Ce_{0.3}$(catalyst B).

The catalyst is prepared from a citric acid solution containing the suitable proportions of copper nitrate, zinc carbonate, cobalt carbonate, cerium carbonate and chromic anhydride. The catalyst is dried at 200° C., then roasted in air at 450° C.

The operating conditions applied in each of these reactors are reported in Table 1. The synthesis gas (whose composition is given in Table 2) at first passes through an isothermal reactor over a fixed bed of 100 g of catalyst A; the produced alcohols are condensed and separated from a gas phase (whose composition is substantially similar to that of the initial synthesis gas) which is heated before passing through a second isothermal reactor over a fixed bed of 44 g of catalyst B. The methanol produced in this second reactor is condensed and the unconverted gas conveyed to the purge line without recycling to the second reactor. In this example also there is no alcohol recycling to the first catalytic zone. The composition of the products obtained at the outlet from the two reactors is given in Table 3.

TABLE 1

| OPERATING CONDITIONS | | |
|---|---|---|
| | 1st REACTOR | 2nd REACTOR |
| P (bars) | 75 | 70 |
| V.V.H. (m³/m³ cata/h) | 4,000 | 8,000 |
| T | 280° C. | 270° C. |

TABLE 2

| MOLAR COMPOSITION OF THE GAS (% mol) | | |
|---|---|---|
| | INLET of 1st REACTOR | INLET of 2nd REACTOR |
| CO | 21 | 20.2 |
| $CO_2$ | 9 | 9.0 |
| $H_2$ | 69 | 69.4 |
| $N_2$ | 1 | 1.1 |
| Alcohols + dimethyl-ether + $CH_4$ | 0 | 0.3 |

TABLE 3

| RESULTS AT THE REACTOR OUTLET | | |
|---|---|---|
| | OUTLET of 1st REACTOR | OUTLET of 2nd REACTOR |
| Conversion (CO + $CO_2$) (%) | 18.3 | 28.4 |
| Hourly productivity (g alcohols/g cata × hour) | 0.231 | 0.89 |
| Composition of liquid products at separators (% weight) | | |
| methanol | 31 | 99 |
| ethanol | 41 | |
| n-propanol | 17 | |
| isopropanol | 2 | 1 |
| n-butanol | 8 | |
| isobutanol | 1 | |

The alcohol effluents are combined and there is obtained a mixture, at a rate of 62.25 g/hour, which contains 25.60% by weight of homolog alcohols and 74.40% of methanol.

EXAMPLE 2

Example 1 is repeated with the same catalysts, the same two reactors and the same synthesis gas. The first reactor still contains 100 g of catalyst A but the second reactor contains 132 g of catalyst B instead of 44 g. Moreover, there is recycled to the second reactor 92% of the unconverted gas from the second reactor. This recycled gas amounts, by volume, to 6% of the gas withdrawn from the first reactor; the second reactor is thus fed with a synthesis gas having, under normal running conditions, the composition indicated in Table 4. The composition of the products obtained at the outlets of the two reactors is given in Table 5.

TABLE 4

| COMPOSITION OF THE GAS (% mol) | | |
|---|---|---|
| | INLET of 1st REACTOR | INLET of 2nd REACTOR |
| CO | 21 | 8.4 |
| $CO_2$ | 9 | 3.6 |
| $H_2$ | 69 | 73 |
| $N_2$ | 1 | 9 |
| Alcohols + dimethyl- | | |

TABLE 4-continued

| COMPOSITION OF THE GAS (% mol) | | |
| --- | --- | --- |
|  | INLET of 1st REACTOR | INLET of 2nd REACTOR |
| ether + $CH_4$ | 0 | 6 |

TABLE 5

| RESULTS AT THE REACTOR OUTLETS | | |
| --- | --- | --- |
|  | OUTLET of 1st REACTOR | OUTLET of 2nd REACTOR |
| Conversion (CO + $CO_2$) (%) | 18.3 | 45 |
| Hourly productivity g alcohols/g cata × hour | 0.231 | 0.84 |
| Composition of liquid products at separators (% weight) | | |
| methanol | 31 | 99 |
| ethanol | 41 |  |
| n-propanol | 17 |  |
| isopropanol | 2 | 1 |
| n-butanol | 8 |  |
| isobutanol | 1 |  |

The total hourly productivity of the produced alcohols collected together is 133.98 g/h, the alcohol mixture containing:
11.9% of homolog alcohols and
88.1% of methanol.

When the 92% gas recycling to the methanol synthesis reactor is omitted, the conversion rate of (CO+$CO_2$) in the methanol synthesis reactors falls to 40%.

Furthermore, when recycling 92% of the gas to the methanol synthesis reactor and also recycling to the reactor for the synthesis of homolog alcohols, 13.4 g/h of methanol, i.e. 4.20% by weight of the total mixture of the alcohols obtained at the end of the process (resulting in the dilution of the initial synthesis gas of about 10%) there is obtained a conversion rate of 18.2% of (CO+$CO_2$) in the synthesis reactor of homolog alcohols and, in this same reactor, there is obtained a production of 0.415 g of alcohols per gram of catalyst and per hour, (the composition of the $C_1$–$C_5$ alcohols being substantially the same as that indicated in Table 5 when not considering the recycled methanol). The gas phase is then fed to the methanol synthesis reactor under the preceding conditions and there is obtained in this reactor, the same results as in Table 5. After removal of water, the alcohols issued from each of the two reactors are admixed and there is so obtained 131.40 g of a mixture containing by weight 19.10% of $C_2$–$C_5$ alcohols and 80.90% of methanol.

EXAMPLE 3

In this example, the catalytic zone or reactor 7 is replaced by two reactors in series. Reactor 22 remains unchanged.

The synthesis gas, having the same composition as in example 1, at first passes through a first reactor containing 100 g of catalyst A. The obtained effluent is cooled and the homolog alcohols are condensed. The gas phase of the effluent (whose composition is very close to that of the initial synthesis gas) is then heated and supplied to a second reactor containing also 100 g of catalyst A. After cooling and separation of the alcohols, the residual gas (whose composition is also close to that of the initial gas) is fed to a third reactor containing 132 g of catalyst B. The methanol produced in this reactor is condensed and the unconverted gas conveyed to the purge line, without recycling to the third reactor. The composition of the gases at the inlet of the three reactors is reported in Table 6 and the composition of the obtained liquid products in Table 7. In this example, the operating conditions of the first and the second reactor are identical to those applied to the first reactor in the preceding examples. The operating conditions of the third reactor are those applied to the second reactor in example 1.

TABLE 6

| COMPOSITION OF THE GASES (% mol) | | | |
| --- | --- | --- | --- |
|  | INLET of 1st REACTOR | INLET of 2nd REACTOR | INLET of 3rd REACTOR |
| CO | 21 | 20.2 | 19.7 |
| $CO_2$ | 9 | 9 | 9.1 |
| $H_2$ | 69 | 69.4 | 69.5 |
| $N_2$ | 1 | 1.1 | 1.3 |
| Alcohols + dimethylether + $CH_4$ | 0 | 0.3 | 0.4 |

TABLE 7

| RESULTS AT THE REACTOR OUTLETS | | | |
| --- | --- | --- | --- |
|  | OUTLET of 1st REACTOR | OUTLET of 2nd REACTOR | OUTLET of 3rd REACTOR |
| Conversion % (CO + $CO_2$) | 18.3 | 17.6 | 32 |
| Hourly productivity g/g cata × hour | 0.231 | 0.213 | 0.73 |
| Composition of liquid products at separators (% weight) | | | |
| methanol | 31 | 31 | 99 |
| ethanol | 41 | 41 |  |
| n-propanol | 17 | 17 |  |
| isopropanol | 2 | 2 | 1 |
| n-butanol | 8 | 8 |  |
| isobutanol | 1 | 1 |  |

The total productivity of the alcohols produced in the three reactors is 140.76 g including 109.16 g of methanol and 31.60 g of homolog alcohols. The total mixture thus contains, by weight, 22.45% of homolog alcohols and 77.55% of methanol.

Furthermore, recycling to third reactor of 92% of the unconverted gas from said third reactor (which corresponds to about 6% of the volume of the gas withdrawn from the second reactor), the conversion rate of CO+$CO_2$ is improved in the same proportion as observed in example 2. The conversion of (CO+$CO_2$) which, without recycling, was 32%, increases to 37%.

EXAMPLE 4

The catalysts are the same as in example 1 and are used in the same amounts as in example 2 and the reactors are the same as in example 1, the operating conditions being those reported in Table 8 below; moreover, methanol is added to the synthesis gas so as to obtain the molar composition shown in Table 9. This methanol is obtained from the mixture of alcohols produced in the first reactor and corresponds to about 4.5% of this mixture (by weight). The product is cooled and separated from the gas phase; the gas phase, whose composition is given in Table 9, is fed, without intermediary compression, to the second reactor containing catalyst B. The composition of the obtained products is reported in Table 10.

TABLE 8

| OPERATING CONDITIONS | | |
|---|---|---|
| | 1st REACTOR | 2nd REACTOR |
| P (bars) | 90 | 85 |
| V.V.H. | 3,000 | 8,000 |
| T | 290° C. | 265° C. |

TABLE 9

| MOLAR COMPOSITION OF THE GAS (%) | | |
|---|---|---|
| | INLET of 1st REACTOR | INLET of 2nd REACTOR |
| CO | 18.9 | 23.0 |
| $CO_2$ | 8.1 | 7.2 |
| $H_2$ | 62.1 | 68.3 |
| $N_2$ | 0.9 | 1.2 |
| Methanol | 10 | |
| Alcohols + dimethyl-ether | | 0.3 |

TABLE 10

| RESULTS AT THE REACTOR OUTLETS | | |
|---|---|---|
| | OUTLET of 1st REACTOR | OUTLET of 2nd REACTOR |
| Conversion (CO + $CO_2$) (%) | 15 | 29 |
| Hourly productivity $C_2$ + g alcohols/g cata × hour | 0.38 (0.21 without methanol) | 0.84 |
| Composition of liquid products at separators (% weight) | | |
| methanol | 44.73 | 99 |
| ethanol | 32.06 (58 without methanol) | |
| n-propanol | 12.72 (23 without methanol) | |
| isopropanol | 1.38 (2.5 without methanol) | 1 |
| n-butanol | 6.35 (11.5 without methanol) | |
| isobutanol | 2.76 (5 without methanol) | |

By collecting together the alcohols produced in the process, there is obtained a total hourly productivity of 148.88 g of alcohols including, by weight, 85.15% of methanol and 14.85% of homolog alcohols.

Furthermore, when recycling to the second reactor 92% of the unconverted gas from said second reactor, the conversion of $CO+CO_2$ is increased to 35.5%.

EXAMPLE 5

There is used, for the synthesis of higher alcohols a catalyst C wherein the metals are in the following atomic proportions:

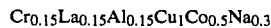

$Cr_{0.15}La_{0.15}Al_{0.15}Cu_1Co_{0.5}Na_{0.3}$

The catalyst is prepared from an aqueous solution containing suitable proportions of chromium nitrate, lanthanum nitrate, copper nitrate, cobalt nitrate, 1 N nitrate solution in which is suspended the suitable amount of an alumina having a specific surface of 200 m²/g and a grain size of 10 to 100μ. Under strong stirring a precipitate is formed by a 0.5 N solution of sodium carbonate.

The precipitate is washed several times and dried at 50° C. for 24 hours; this precipitate is then impregnated with a solution of sodium acetate whose concentration has been so adjusted as to obtain the desired sodium content of the catalyst.

After drying for 6 hours at 120° C., the product is treated for 6 hours at 400° C. in air; the resulting powder is pelletized to pellets of a 5 mm diameter and a 5 mm height.

For the synthesis of methanol, there is used a catalyst D wherein the metals are in the following atomic proportions:

$Cu_1Co_{0.5}Zn_{0.2}Mn_{0.2}Cr_{0.2}La_{0.2}$

The catalyst is prepared from a 0.1 N citric acid solution containing a 1 N solution of the different nitrates. The catalyst is dried at 200° C. and then roasted in air at 450° C. for 4 hours.

In the reactor for the synthesis of higher alcohols, which contains 100 ml of catalyst C amounting to a weight of 98 g and which is operated at a pressure of 85 bars and a temperature of 295° C., there is passed 400 liters per hour of a gas whose composition is identical to that supplied at the inlet of the first reactor in example 1 (V.V.H.: 4000 m³/m³ cata/h).

The gas phase, after separation by condensation of the formed alcohols and water, is fed to a second reactor for methanol synthesis which contains 130 ml of a catalyst D amounting to a weight of 141 g. As in example 2, there is recycled 92% of the gases issued from the methanol synthesis reactor to this reactor.

The composition of the liquid products obtained at the outlet of the reactor for the synthesis of homolog alcohols is reported in Table 11. The composition of the gas phase issued from this reactor for the synthesis of homolog alcohols, after condensation of the liquid phase, is substantially identical to that of example 1. However the methanol content in this case is 0.5%.

The composition of the liquid phase obtained in the reactor for the methanol synthesis is also given in Table 11.

TABLE 11

| RESULTS AT THE REACTOR OUTLETS | | |
|---|---|---|
| | OUTLET of 1st REACTOR | OUTLET of 2nd REACTOR |
| Conversion (CO + $CO_2$) % | 18 | 52 |
| Hourly productivity g/alcohols/ml cata × hr | 0.226 | 0.96 g |
| Hourly productivity g/various alcohols/ml cata hr | | |
| Methanol | 0.0746 (33.00%) | 0.95 |
| Ethanol | 0.0701 (31.03%) | <0.01 |
| Propanol | 0.0362 (16.02%) | " |
| Isopropanol | 0.0067 (2.96%) | " |
| Butanol | 0.0237 (10.49%) | " |
| Isobutanol | 0.0055 (2.43%) | " |
| n-pentanol | 0.0090 (3.98%) | " |

After water removal, the alcohols issued from each of the two reactors are admixed without separating the different alcohols obtained in the first reactor and there is so obtained, per hour, (0.226×100 ml+0.96×130 ml) g of alcohols, i.e. 147.5 g of a mixture of alcohols containing 10.3% by weight of $C_2$-$C_5$ alcohols and 89.7% of methanol.

When the recycling of the gas from the reactor for the methanol synthesis to said reactor is omitted, the conversion rate of ($CO+CO_2$) falls to 48%.

EXAMPLE 6

The nature and the amounts of catalyst are identical to those of example 5, as well as the various operating conditions except that there is recycled to the inlet of the reactor for the synthesis of higher alcohols, in the liquid state, a mixture of 22 g/hour of methanol with 4.11 g of ethanol withdrawn from the alcohol mixture obtained in the process, this mixture amounting to 17.6% of obtained total mixture of alcohols.

In these conditions, and taking into consideration the amount of alcohols introduced, there is obtained, in this reactor, an hourly productivity of various alcohols, expressed in gram per ml of catalyst, of 0.431, with the following distribution:

| | | |
|---|---|---|
| methanol | 0.1628 | (37.77%) |
| ethanol | 0.1253 | (29.09%) |
| propanol | 0.0637 | (14.78%) |
| isopropanol | 0.0071 | (1.65%) |
| butanol | 0.0509 | (11.82%) |
| i-butanol | 0.0060 | (1.39%) |
| n-pentanol | 0.0151 | (3.50%) |

The conversion rate of $CO+CO_2$ is 17.9% in this reactor for the synthesis of homolog alcohols.

The methane content of the gas phase, at the outlet of this reactor and after condensation, is 0.1%. It can be seen that the recycling of alcohol (in this case: methanol and ethanol) strongly increases the productivity of $C_2-C_5$ alcohols with a substantially equal conversion rate of the gas phase $CO+CO_2$ and results in a substantial reduction of the methanation reaction.

The gas phase is then fed, as in example 5, to the reactor for methanol synthesis under the same operating conditions and by proceeding to the same gas recycling as in said example 5.

The composition of the liquid phase and the conversion in this reactor are identical to those of example 5. After removal of water the alcohols issued from each of the two reactors are admixed and there is so obtained 141.8 g of a mixture containing 16% by weight of $C_2-C_5$ alcohols and 84% of methanol.

What is claimed is:

1. A process for manufacturing a mixture of methanol and saturated, mainly linear primary homolog alcohols, said mixture being suitable for direct use as a component of automotive gasoline, said process comprising the steps of:
   (1) passing a synthesis gas comprising carbon dioxide, carbon monoxide and hydrogen through a first catalytic zone, at a temperature of 230°–350° C., under conditions favoring the synthesis of a mixture of methanol and saturated, mainly linear primary homolog alcohols;
   (2) cooling the resultant effluent, separating the resultant liquid phase from the unconverted gas phase, and removing water from the liquid phase to produce a first liquid phase containing methanol and a mixture of saturated, mainly linear primary homolog alcohols comprising mainly ethanol and propanol;
   (3) passing at least a portion of the separated gas phase from step (2) through a second catalytic zone, at a temperature of 240°–300° C., under conditions favoring the synthesis of only methanol;
   (4) cooling the effluent from the second catalytic zone, separating the resultant liquid phase from the unconverted gas phase, and removing water from the liquid phase to produce a second liquid phase containing at least about 97% by weight of methanol; and
   (5) combining said first liquid phase with said second liquid phase to produce a product mixture containing 74–90% by weight of methanol and 10–26% by weight of saturated, mainly linear primary homolog alcohols; said product mixture being suitable for direct use as a component of automotive gasoline.

2. A process according to claim 1, wherein the molar composition of the gas withdrawn from the first catalytic zone is substantially close to the composition of the synthesis gas fed to the first catalytic zone.

3. A process according to claim 1, wherein the molar ratio ($H_2/CO+CO_2$) of said synthesis gas is from 0.5 to 4 and wherein the CO conversion rate in the first catalytic zone is from 7 to 40% with respect to the gas feed at the inlet of said first reaction zone.

4. A process according to claim 1, wherein the production of homolog alcohols in said first catalytic zone is increased by forming a recycle alcohol stream comprising an alcohol or a mixture of alcohols selected from the group consisting of (a) methanol produced in the first catalytic zone, (b) a mixture of the methanol produced in the first catalytic zone with at least one homolog alcohol produced in the first catalytic zone, (c) methanol separated from the total mixture of the alcohols produced in the process of the invention, (d) a portion of the total mixture of the alcohols produced in the process of the invention (e) at least one homolog alcohol produced in the first catalytic zone and (f) methanol produced in the second catalytic zone; and recycling said recycle alcohol stream to said first catalytic zone.

5. A process according to claim 1, wherein at least a portion of the unconverted gas phase separated from the effluent of the second catalytic zone is recycled back to said second catalytic zone.

6. A process according to claim 1, wherein the catalyst in said first catalytic zone comprises copper; cobalt; at least one element M selected from chromium, iron, vanadium, manganese and a rare earth; and at least one alkali metal A; the elements being present in the following atomic proportions: $Cu_x\ Co_y\ M_z\ A_v$, wherein x is from 0.1 to 1; y is from 0.1 to 1; z is from 0.2 to 1; and v is from 0.001 to 0.25 times the sum $(x+y+z)$.

7. A process according to claim 6, wherein at least a portion of the unconverted gas phase separated from the effluent of the second catalytic zone is recycled back to said second catalytic zone.

8. A process according to claim 7, wherein the recycling is effected by introducing said portion of the unconverted gas phase at one or more points as a quench in said second catalytic zone.

9. A process according to claim 1, wherein said first catalytic zone consists of at least two catalytic chambers arranged in series, and wherein the effluent withdrawn from each catalytic chamber is freed from the higher homologs of methanol contained therein before being fed to the next catalytic chamber, the molar ratio ($H_2/CO+CO_2$) being from 0.5 to 4 at the inlet of each catalytic chamber.

10. A process according to claim 1 wherein the first catalytic zone is operated at a temperature $T_1$ from about 265° to 300° C. and the second catalytic zone at a temperature $T_2$ from 260° to 270° C., the temperature $T_2$ being lower by about 5° to 30° C. than temperature $T_1$.

11. A process according to claim 1, wherein the catalyst in said second catalytic zone comprises copper; cobalt; zinc; and at least one metal M selected from chromium, iron, vanadium, manganese or a rare earth, in the following atomic proportions:

$Cu_{x'}Co_{y'}Zn_{u'}M_{z'}$ wherein x' is from 0.1 to 1; y' is from 0.01 to 0.2; u' is from 0.1 to 1; and z' is from 0.2 to 2.

12. A process according to claim 6, wherein the catalyst further comprises a carrier.

13. A process according to clam 12, wherein said carrier is alumina or calcium aluminate.

14. A process according to claim 6, wherein in step (1), the pressure in said first catalytic zone is 30-150 bars, and the space velocity is 1,000-10,000 Nm³ of synthesis gas per m³ of catalyst per hour.

15. A process according to claim 6, wherein in step (1), the pressure in said first catalytic zone is 50-20 bars, and the space velocity is 2,000-6,000 Nm³ of synthesis gas per m³ of catalyst per hour.

16. A process according to claim 6, wherein said catalyst further contains zinc, in the atomic proportion $Zn_u$, wherein u is 0-0.5 and not more than 0.5y.

17. A process according to claim 1, wherein in step (3), the pressure in said second catalytic zone is 50-120 bars, and the space velocity is 5,000-20,000 Nm³ of gas phase per m³ of catalyst per hour.

18. A process according to claim 1, wherein in step (3), the molar ratio $H_2/(CO+CO_2)$ is 1.5-10.

19. A process according to claim 11, wherein said catalyst further comprises a carrier.

20. A process according to claim 19, wherein said carrier contains alumina.

* * * * *